US007649103B2

(12) United States Patent
Cravotto

(10) Patent No.: US 7,649,103 B2
(45) Date of Patent: Jan. 19, 2010

(54) LONG CHAIN UNSATURATED OXYGENATED COMPOUNDS AND THEIR USE IN THE THERAPEUTICAL, COSMETIC AND NUTRACEUTICAL FIELD

(75) Inventor: Giancarlo Cravotto, Turin (IT)

(73) Assignee: Medestea Research and Production S.r.l., Colleretto Giacosa (IT)

( * ) Notice: Subject to any disclaimer, the term of this patent is extended or adjusted under 35 U.S.C. 154(b) by 496 days.

(21) Appl. No.: 10/518,091

(22) PCT Filed: Jun. 16, 2003

(86) PCT No.: PCT/IB03/02317

§ 371 (c)(1),
(2), (4) Date: Dec. 16, 2004

(87) PCT Pub. No.: WO03/105822

PCT Pub. Date: Dec. 24, 2003

(65) Prior Publication Data

US 2005/0234127 A1    Oct. 20, 2005

(30) Foreign Application Priority Data

Jun. 17, 2002  (IT) .......................... TO2002A0521
Dec. 3, 2002   (IT) .......................... TO2002A1049

(51) Int. Cl.
*C07C 57/00* (2006.01)

(52) U.S. Cl. ...................... 554/224; 554/227; 514/547; 514/560; 568/840

(58) Field of Classification Search ................. 554/223, 554/224, 227; 514/560, 739, 873, 875, 547
See application file for complete search history.

(56) References Cited

U.S. PATENT DOCUMENTS 4,950,688 A * 8/1990 Bowser et al. .............. 514/560

5,502,077 A    3/1996  Breivik et al.
5,656,667 A    8/1997  Breivik et al.

(Continued)

FOREIGN PATENT DOCUMENTS

EP    1 106 181    6/2001

OTHER PUBLICATIONS

Chem. Abstr. of JP-60/218328 with registry number, 1984.*

(Continued)

*Primary Examiner*—Deborah D Carr
(74) *Attorney, Agent, or Firm*—Roylance, Abrams, Berdo & Goodman, L.L.P.

(57) ABSTRACT

Long-chain unsaturated oxygenated compounds and their use in the therapeutical, cosmetic and nutraceutical field. Use of compounds of formula R—X wherein X is a primary alcoholic functional group —$CH_2OH$, a carboxylic functional group —COON or a C1-C4 alkyl ester group, and of mono-, di- and tri-glycerides of acid compounds R—COON and of pharmaceutically acceptable salts of those acids, wherein R is a hydrocarbon chain having from 19 to 35 carbon atoms, which is saturated or unsaturated, including from one to five ethylenic or acetylenic unsaturations, linear or branched, including from one to five methyl branches, and optionally substituted by from one to three hydroxyl groups, for the preparation of pharmaceutical or nutraceutical compositions useful for the treatment and prevention of pathologies related to a high concentration of cholesterol and lipids, pathologies associated with an increased ability of the blood platelets to aggregate and with a reduced concentration of oxygen, in the treatment of ageing processes, for the preparation of compositions of nutritional integrators aimed at weight loss and cosmetic compositions useful in the treatment and prevention of skin damage caused by free radicals.

10 Claims, 1 Drawing Sheet

Figure 1:
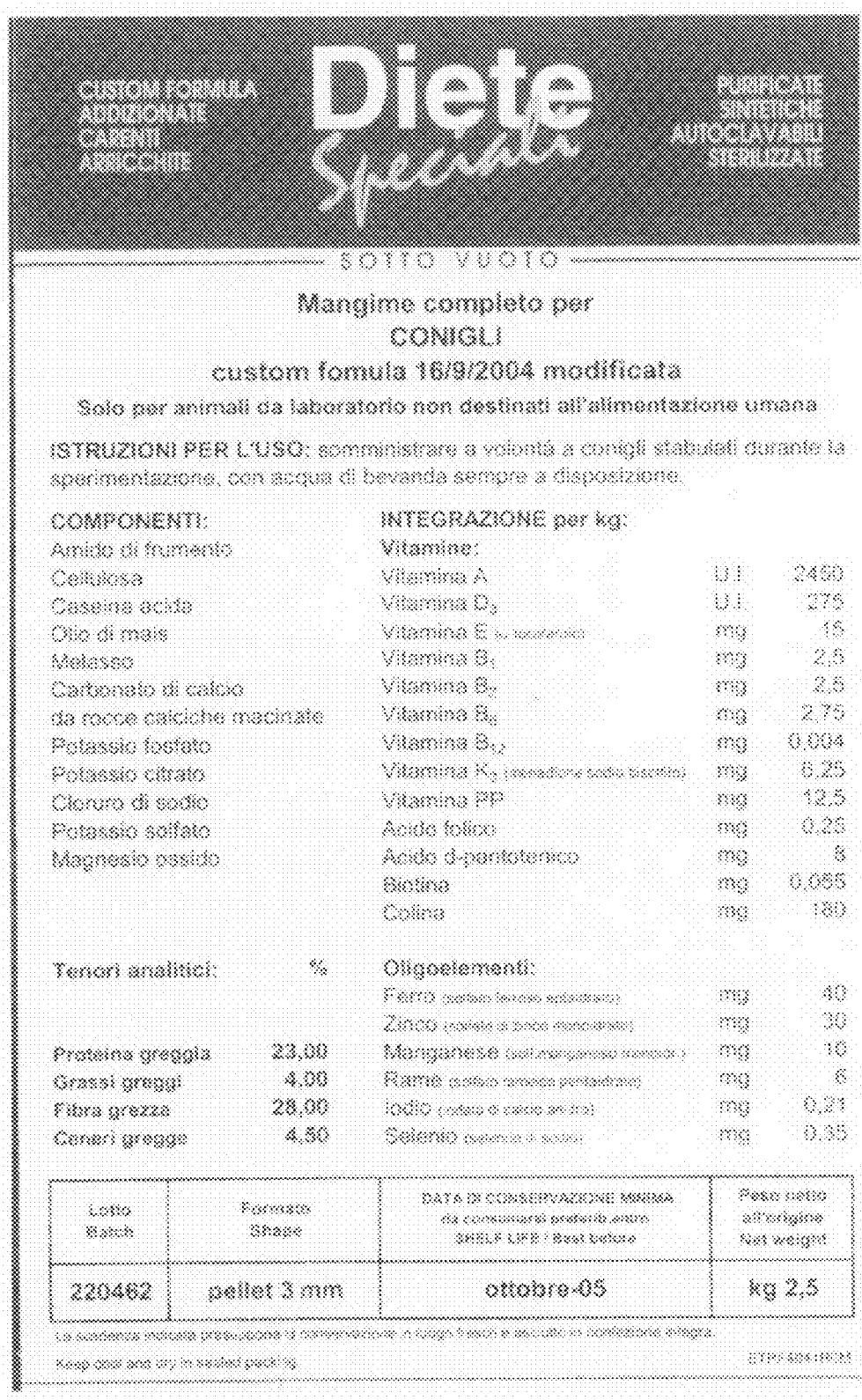

U.S. PATENT DOCUMENTS 5,698,594 A     12/1997  Breivik et al.
6,328,998 B1 *  12/2001  Cavazza .................... 424/725
6,656,662 B1 *  12/2003  Okawa et al. .............. 430/296

OTHER PUBLICATIONS

Chem. Abstr. DN 100:120506.*

Murakami et al., Japanese Journal of Pharmacology, vol. 33, No. 3, pp. 549-556, 1983.*
Japanese Patent Abstr., JP 58144317, 1983.*
Chem. Abstracts DN 119:249724.
Chem. Abstracts DN 114:202299.
Chem. Abstracts DN 100:120506.

* cited by examiner

LONG CHAIN UNSATURATED OXYGENATED COMPOUNDS AND THEIR USE IN THE THERAPEUTICAL, COSMETIC AND NUTRACEUTICAL FIELD

The present invention relates to novel uses in the therapeutic, cosmetic and nutraceutical field of alcohols, acids and esters of those acids having a long mono- or poly-unsaturated hydrocarbon chain.

The novel uses and the compounds forming the subject-matter of the invention are defined in the claims which follow.

In particular, the novel uses to which the invention relates concern compounds of formula R—X, wherein X is an optionally salified primary alcoholic —$CH_2OH$ or carboxylic —COOH functional group or an esterified carboxylic group —$COOR_3$, wherein $R_3$ is $C_1$-$C_4$ alkyl, preferably ethyl or propyl (and glyceride esters of those acids), and wherein R is a hydrocarbon chain having from 19 to 35 carbon atoms, preferably from 23 to 35 and more preferably from 25 to 31 carbon atoms, and including one or more ethylenic or acetylenic unsaturations, preferably from one to five unsaturations; the hydrocarbon chain R is preferably a linear or, optionally, a branched chain, including from one to five methyl branches, which chain may optionally be substituted by one or more hydroxy groups, for example, by from one to three hydroxy groups.

The invention is also directed to a preferred class of compounds which is constituted by compounds of the general formula $R_2=R_1$—X, wherein X has the meaning mentioned above and wherein $R_1$ and $R_2$ have a total of from 23 to 35 carbon atoms, preferably from 25 to 31 carbon atoms, and $R_1$ is a saturated linear hydrocarbon chain having from 4 to 15, preferably from 7 to 13 carbon atoms and $R_2$ is a hydrocarbon chain having from 8 to 22, preferably from 10 to 20 carbon atoms, which is saturated or unsaturated, including from one to four ethylenic or acetylenic unsaturations, and preferably linear or optionally branched, including from one to four methyl branches, and optionally substituted by hydroxy, for example, by from one to three hydroxy groups.

Even more preferred are compounds wherein $R_1$ is a linear saturated hydrocarbon chain having 9 carbon atoms and compounds wherein $R_2$ is the hydrocarbon chain of a saturated or unsaturated naturally occurring fatty acid, such as, for example, the hydrocarbon chain of oleic, lineoleic, linolenic, ricinoleic or farnesylic acid.

The compounds according to the invention can be prepared by synthesis processes known in the literature, in particular by the process described in TO2002A000521 in the name of the applicant, the description of which is to be regarded as incorporated herein by reference.

This process comprises a Wittig olefination reaction (cf. Merck Index, XII ed., ONR-99 and references mentioned therein) in which a phosphorus ylide ($R''P(Ar)_3$)—wherein R" is a saturated or unsaturated hydrocarbon chain including one or more ethylenic or acetylenic unsaturations and wherein Ar is phenyl—is reacted with an n-alkanoic acid R'COOH oxo-substituted in the terminal position or with the $C_1$-$C_4$ alkyl ester of that oxo-substituted alkanoic acid to give the addition product constituted by the alkenoic acid R"=R'—COOH or its alkyl ester (where the term alkenoic refers to the presence of the ethylenic unsaturation introduced as a result of the Wittig reaction), having the desired chain length.

The number of carbon atoms in the group RN of the above-mentioned phosphorus ylide may vary within wide limits and in particular R" may coincide with the group $R_2$ defined above.

Similarly, the length of the chain R' of the above-mentioned n-alkanoic acid, which is formylated in the terminal position, or its alkyl ester may vary within wide limits and may be selected as a function of the position in which the desired compound has the first double bond.

In particular R' may have a number of carbon atoms corresponding to the definition of $R_1$ given above and more particularly may be 10-oxo-decanoic acid or the corresponding lower alkyl (preferably ethyl) 10-oxo-decanoate.

The phosphorus ylide $R''P(Ar)_3$ is prepared by reacting the corresponding halogen derivative (where halogen is preferably bromine or chlorine) with triphenylphosphine, preferably in an aromatic solvent (toluene) while heating under reflux; at the end of the reaction, the solution is concentrated and the phosphonium salt is precipitated, preferably with ether.

Because in the Wittig reaction described above it is preferable to use as reagent the alkyl ester, formylated in the terminal position, of an n-alkanoic acid, the process leads directly to the preparation of unsaturated compounds, used within the scope of the invention, having an ester functionality. The corresponding unsaturated acids can be obtained from the ester by alkaline hydrolysis and the corresponding compounds having a primary alcohol functionality by reduction of the ester, for example, with lithium aluminium hydride.

In one embodiment, the composition of the invention includes a compound selected from the group consisting of octacosa-10,19-dienoic acid, octacosa-10,19,22-trienoic acid, octacosa-10,19,22,25-tetraenoic acid, 14,18,22-trimethyltricosa-10,13,17,21-tetraenoic acid, primary alcohols of 10,19 octacosadiene, 10,19,22 octacosatriene, 10,19,22,25 octacosatetraene and 14,18,22 trimethyltricosa-10,13,17,21 tetraene, and $C_1$-$C_4$ esters of octacosa-10,19-dienoic acid, octacosa-10,19,22-trienoic acid, octacosa-1,19,22,25-tetraenoic acid, and 14,18,22-trimethyltricosa-10,13,17,21-tetraenoic acid.

The process for preparing compounds used within the scope of the invention is further illustrated by the following Examples.

EXAMPLE 1

Preparation of the ethyl ester of octacosa-10,19-dienoic acid

The synthesis process is illustrated in the following scheme and the associated operating stages are described in Examples 1a-1d which follow.

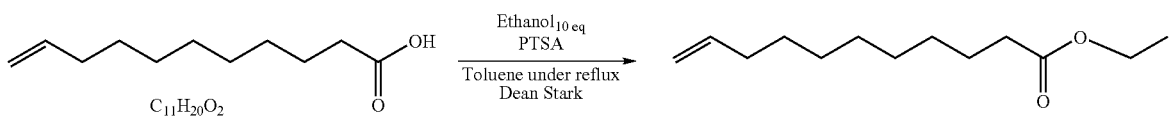

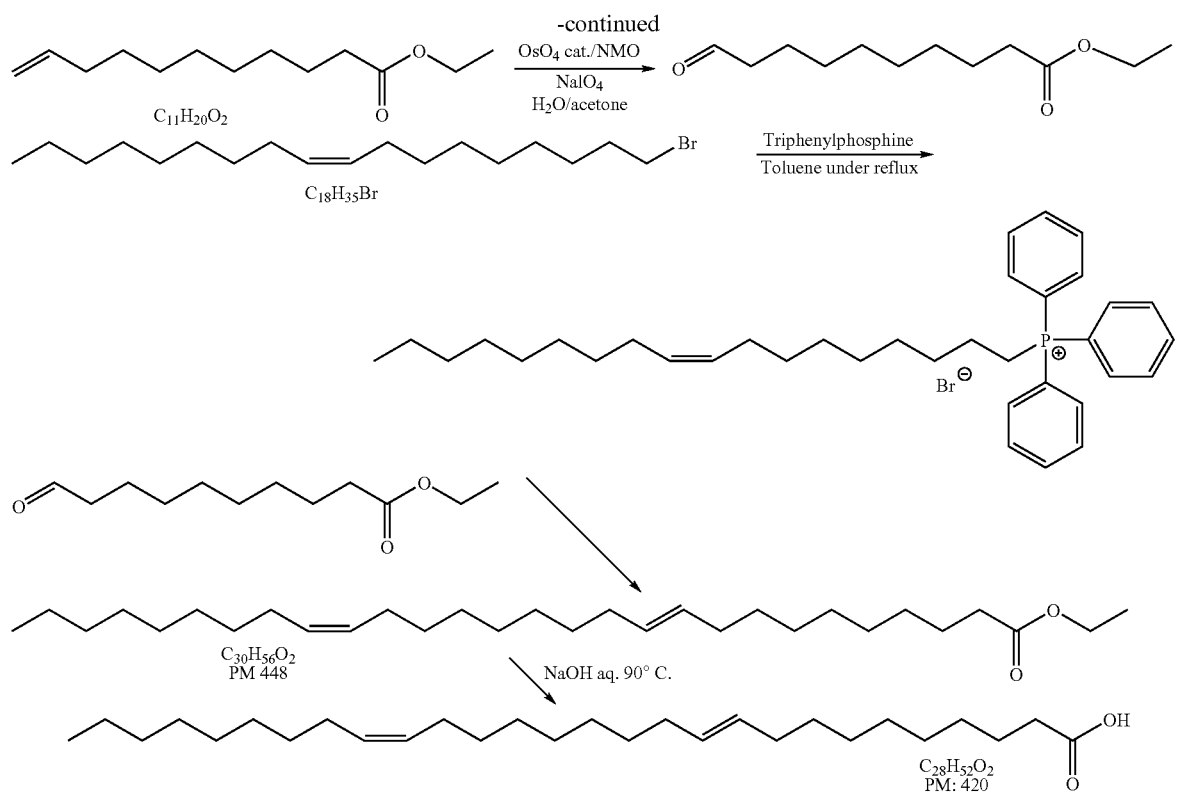

NMO: N-methylmorpholine N-oxide

EXAMPLE 1a

Ethyl ester of undecylenic acid

In a 100 ml two-necked flask, 8 ml of ethanol and a spatula tip of p-toluenesulphonic acid are added to 15 g of undecylenic acid (81.4 mmol) dissolved in 35 ml of anhydrous toluene. The whole is heated under reflux for 8 hours with a Dean Stark or Markusson distilling apparatus separating the water of esterification. All of the glassware used has previously been dried in an oven at 120° C. The progress of the reaction is monitored by TLC (silica gel plates), eluant hexane/EtOAc 7:3. $R_f$ ester=0.67.

Work-up: the product is diluted with EtOAc, washed twice with a mixture of $NaHCO_3/H_2O$ 1:1, then with $H_2O$ and a saturated NaCl solution and dried over $Na_2SO_4$. 16.7 g (78.9 mmol) are obtained (Yield 97%). Any traces of starting acid can be eliminated by filtration over a bed of alumina.

EXAMPLE 1b ethyl 10-oxodecanoate

In a 500 ml flask, 2.5 ml of a 0.2 M solution of 0504 in toluene (0.005 eq; 1.03 mmol) and 24.13 g of N-methylmorpholine-N-oxide (1 eq) are added to 43.67 g of the ethyl ester of undecylenic acid (0.206 mmol) dissolved in 100 ml of a 1:1$H_2O$/acetone mixture. The whole is left under agitation for fifteen minutes at 0° C. in ice. 79.31 g of $NaIO_4$ (1.8 eq; 0.37 mmol) are then added in small portions over a period of 40 minutes at ambient temperature. The reaction is followed by TLC (silica gel plates), eluant hexane/EtOAc 7:3 $R_f$ product=0.5.

Work-up: the product is filtered on a funnel having a sintered porous baffle, diluted with EtOAc, washed with a saturated NaCl solution and dried over $Na_2SO_4$. The product is then purified on a chromatographic column of silica gel (CC) eluant hexane/EtOAc 9:1. 38.3 g of ethyl 10-oxo-decanoate (179.2 mmol) are obtained. (Yield 87%).

EXAMPLE 1c

Phosphonium salt of cis 1-bromo-9-octadecene

In a 250 ml flask, 1 eq of triphenylphosphine (24.6 g) is added to 29.8 g of cis 1-bromo-9-octadecene (0.09 mmol) dissolved in 80 ml of anhydrous toluene. The whole is heated under reflux in a heating jacket for 24 hours. It is cooled in a bath of water and ice for approximately 10 minutes and then approximately 15 ml of diethyl ether are added. The phosphonium salt precipitates in abundance and is filtered on a funnel having a sintered porous baffle and is washed with approximately 50 ml of ether. 40.9 g of a pearly pink solid (71.2 mmol) are obtained. (Yield 80%).

EXAMPLE 1d

Ethyl ester of octacosa-10,19-dienoic acid

In a 1 l two-necked flask, 31.9 g of phosphonium salt (56.0 mmol) are dissolved in 350 ml of anhydrous THF with magnetic agitation in a nitrogen atmosphere. All the glassware used has previously been dried in an oven at 120° C. 1.05 eq of BuLi solution (1.6 M in hexane) (34 ml) are slowly added dropwise; the reaction mixture progressively becomes an orange-red colour, which indicates the formation of the ylide. After approximately 20 minutes, 5 ml of a solution containing 10.78 g of ethyl 10-oxo-decanoate (0.9 eq; 50.4 mmol) are slowly added dropwise; during the addition of the aldehyde, the colour of the solution becomes yellow-orange. The whole is left under magnetic agitation overnight. The reaction is monitored by TLC (silica gel plates), eluant hexane/EtOAc 9:1. $R_f$ product=0.67.

Work-up: the product is diluted with a 0.1N HCl solution and extracted with EtOAc; washing is effected with a saturated NaCl solution and drying is effected over $Na_2SO_4$. 20.2 g of product (45.1 mmol) are obtained. (Yield 90%).

EXAMPLE 2

Octacosa-10,19-dienoic acid

In a 100 ml flask, 5.3 g of the ethyl ester of octacosa-10,19-dienoic acid (11.8 mmol) in admixture with an aqueous 3.5N NaOH solution (30 ml) are heated at 90° C. for 2 hours. The reaction is monitored by TLC (silica gel plates), eluant hexane/EtOAc 8:2. $R_f$ product=0.30.

Work-up: the mixture is acidified with 1N HCl and extracted with $CH_2Cl_2$. The organic phase is washed with a saturated NaCl solution and dried over $Na_2SO_4$. 4.7 g of octacosa-10,19-dienoic acid (11.2 mmol) are obtained. (Yield 95%).

EXAMPLE 3

Octacosa-10,19-dienol

The alcohol mentioned above can be obtained from the ethyl ester of octacosa-10,19-dienoic acid (Example 1d) by reduction, for example with lithium aluminium hydride.

EXAMPLE 4

Octacosa-10,19,22-trienoic acid

The acid mentioned above, its corresponding ester (preferably ethyl ester) and the corresponding primary alcohol can be prepared by following the procedure described in Examples 1-3, using as reagent in the Wittig reaction the phosphonium salt of 1-bromo-9,12-octadecadiene (derivative of linoleic alcohol).

EXAMPLE 5

Octacosa-10,19,22,25-tetraenoic acid

The acid mentioned above, its corresponding ester (preferably ethyl ester) and the corresponding primary alcohol can be prepared by following the procedure described in Examples 1-3, using as the starting compound in the Wittig reaction the phosphonium salt of 1-bromo-9,12,15-octadecatriene (derivative of linolenic alcohol).

EXAMPLE 6

14,18,22-trimethyltricosa-10,13,17,21-tetraenoic acid

The acid mentioned above, its corresponding ester (preferably ethyl ester) and the corresponding primary alcohol can be prepared by following the procedure of Examples 1-3, using in the Wittig reaction the phosphonium salt of 1-bromo-3,7,11-trimethyl-2,6,10-dodecatriene (derivative of farnesol).

In general, the compounds described have a better activity than do the corresponding polycosanols and polycosanoic acids and can therefore be used advantageously in the pharmaceutical, cosmetic and nutritional field (particularly for dietetic nutritional integrators) in which the polycosanols and polycosanoic acids are typically used.

The compounds described have a high degree of anti-oxidant activity and a high degree of activity in the capture of free radicals, which enables them to be used both in cosmetic and nutritional compositions as anti-oxidants, in order to prevent the oxidative deterioration of those compositions, and in cosmetic and dermatological compositions for topical use, for the prevention and treatment of skin damage caused by free radicals, such as, in particular, for the treatment and prevention of inflammatory and ageing effects of the skin.

The compounds are also characterized by a higher hypocholesterolaemic and/or hypolipidaemic activity in addition to a favourable effect on the lipoprotein picture (increase in HDL) compared with the corresponding polycosanols; they are therefore suitable for use in the preparation of medicaments and pharmaceutical compositions useful for the treatment and prevention of pathologies related to hypercholesterolaemia and hyperlipidaemia, such as, for example, cardiovascular diseases of the ischaemic or atherosclerotic type and peripheral vascular diseases, and also for the prevention and cure of pathologies associated with an increased ability of the blood platelets to aggregate and with reduced oxygenation and nutrition of tissue, such as, for example, peripheral neuropathies and, in particular, diabetic peripheral neuropathy.

The compounds described have exhibited a high degree of activity in restoring the membrane fluidity of ghost cells or blood platelets and in improving the anti-oxidant defences of the plasma, liver, brain and heart.

Pharmaceutical compositions containing those compounds are therefore useful in general in the treatment of ageing processes, including cerebral ageing and degenerative brain diseases, such as Alzheimer's disease, Parkinson's disease, senile dementia, loss of memory and confused states, and also conditions of stress and depression.

A further use of the compounds described is in the therapeutic treatment and the prevention of obesity, and also in compositions of dietetic nutritional integrators aimed at weight loss and the prevention and treatment of cellulite.

The compounds described can also be used in the preparation of compositions of nutritional integrators intended for strengthening muscle and suitable for increasing physical fitness in humans and animals.

The forms of administration for pharmaceutical compositions and dietetic integrators are preferably forms of administration by the oral route, such as, in particular, tablets, pastilles and capsules, including vehicles and/or excipients that are pharmaceutically acceptable and for nutritional use.

The compounds can also be used in compositions comprising other active ingredients, in particular anti-oxidant vitamins, such as vitamin E, lipoic acid, vitamin C, vitamin B6, vitamin B12.

Also useful is the utilisation of the compounds in association with L-carnitine or an alkanoyl derivative thereof, particularly in the treatment of the above-mentioned pathologies caused by altered lipid metabolism.

The compounds having an acid functionality may be used in the form of pharmaceutically acceptable salts or in the form of tri-, di- and mono-glycerides, esters of phospholipids or also as salts with amino acids (such as, for example, arginine, lysine, methionine, cysteine and the like).

The invention claimed is:

1. A pharmaceutical, nutraceutical, dietetic integrator composition, comprising: a compound of the general formula $R_2=R_1-X$, wherein X is a primary alcoholic functional group —$CH_2OH$, a carboxylic functional group —COOH or a $C_1$-$C_4$ alkyl ester group, wherein $R_1$ and $R_2$ have a total of from 23 to 35 carbon atoms and $R_1$ is a saturated linear hydrocarbon chain having from 4 to 15 carbon atoms and $R_2$ is a linear hydrocarbon chain having from 8 to 22 carbon atoms which is saturated or unsaturated having from one to four ethylenic unsaturations, their pharmaceutically acceptable salts and mono-, di- and tri-glycerides of acids $R_2=R_1$—COOH, and a pharmaceutically acceptable excipient in a form suitable for oral administration.

2. The composition according to claim 1, wherein $R_1$ is a hydrocarbon chain having from 7 to 13 carbon atoms and $R_2$ is a hydrocarbon chain having from 10 to 20 carbon atoms.

3. The composition according to claim 1, wherein $R_1$ is a saturated linear hydrocarbon chain having 9 carbon atoms.

4. The composition according to claim 1, wherein $R_2$ is the hydrocarbon chain of a naturally occurring fatty acid.

5. A pharmaceutically, nutraceutical, dietetic integrator composition comprising:
  a compound selected from the group consisting of:
    octacosa-10,19-dienoic acid,
    octacosa-10,19,22-trienoic acid,
    octacosa- 1,19,22,25-tetraenoic acid,
    14,18,22-trimethyltricosa-10,13,17,21-tetraenoic acid,
    primary alcohols of 10,19 octacosadiene, 10,19,22 octacosatriene, 10,19,22,25 octacosatetraene and 14,18,22 trimethyltricosa 10,13,17,21 tetraene, and
  $C_1$-$C_4$ alkyl ester of
    octacosa-10,19-dienoic acid,
    octacosa-10,19,22-trienoic acid,
    octacosa-10,19,22,25-tetraenoic acid, and
    14,18,22-trimethyltricosa-10,13,17,21-tetraenoic acid,
    and a pharmaceutically acceptable excipient for nutritional use in a suitable form for oral administration.

6. The composition according to claim 5, wherein the $C_1$-$C_4$ alkyl ester is an ethyl ester.

7. The pharmaceutical, nutraceutical, dietetic integrator or cosmetic compositions as defined in claim 1 further comprising anti-oxidant vitamins, carnitine or its alkanoyl derivative.

8. A method of treating hypercholesterolemia comprising administering to a patient an oral pharmaceutical composition comprising a compound having the formula $R_2=R_1-X$, wherein X is a primary alcoholic functional group —$CH_2OH$, a carboxylic functional group —COOH or a $C_1C_4$ alkyl ester group, wherein $R_1$ and $R_2$ have a total of from 23 to 35 carbon atoms and $R_1$ is a saturated linear hydrocarbon chain having from 4 to 15 carbon atoms and $R_2$ is a linear hydrocarbon chain having from 8 to 22 carbon atoms which is saturated or unsaturated having from one to four ethylenic, their pharmaceutically acceptable salts and mono-, di- and tri-glycerides of acids $R_2=R_1$—COOH, and a pharmaceutically acceptable excipient in a suitable form for oral administration.

9. A method for treating hypercholesterolemia comprising administering to a patient an oral pharmaceutical composition comprising a compound selected from the group consisting of:
    octacosa-10,19-dienoic acid,
    octacosa-10,19,22-trienoic acid,
    octacosa- 1,19,22,25-tetraenoic acid,
    14,18,22-trimethyltricosa-10,13,17,21-tetraenoic acid,
    primary alcohols of 10,19 octacosadiene, 10,19,22 octacosatriene, 1,19,22,25 octacosatetraene and 14,18,22 trimethyltricosa 10,13,17,21 tetraene, and
  $C_1$-$C_4$ alkyl ester of
    octacosa-10,19-dienoic acid,
    octacosa-10,19,22-trienoic acid,
    octacosa-1,19,22,25-tetraenoic acid, and
    14,18,22-trimethyltricosa-10,13,17,21-tetraenoic acid
    a pharmaceutically acceptable excipient in a suitable form for oral administration.

10. The composition of claim 1, wherein $R_2$ is a linear unsaturated hydrocarbon chain having 8-22 carbon atoms with one ethylenic double bond.

* * * * *